US011998264B2

(12) United States Patent
Byrd et al.

(10) Patent No.: US 11,998,264 B2
(45) Date of Patent: Jun. 4, 2024

(54) MEDICAL CATHETERS, SYSTEMS INCLUDING MEDICAL CATHETERS, AND METHODS OF POSITIONING MEDICAL CATHETERS

(71) Applicant: St. Jude Medical, Cardiology Division, Inc., St. Paul, MN (US)

(72) Inventors: Israel Byrd, Richfield, MN (US); Greg Olson, Elk River, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 173 days.

(21) Appl. No.: 16/635,298

(22) PCT Filed: Aug. 17, 2018

(86) PCT No.: PCT/IB2018/056219
§ 371 (c)(1),
(2) Date: Jan. 30, 2020

(87) PCT Pub. No.: WO2019/035071
PCT Pub. Date: Feb. 21, 2019

(65) Prior Publication Data
US 2020/0367964 A1  Nov. 26, 2020

Related U.S. Application Data

(60) Provisional application No. 62/547,502, filed on Aug. 18, 2017.

(51) Int. Cl.
*A61B 18/14* (2006.01)
*A61B 34/20* (2016.01)
*A61B 18/00* (2006.01)

(52) U.S. Cl.
CPC .......... *A61B 18/1492* (2013.01); *A61B 34/20* (2016.02); *A61B 2018/00357* (2013.01);
(Continued)

(58) Field of Classification Search
CPC ........ A61B 18/1492; A61B 2018/1407; A61B 2018/00357; A61B 2018/00375
See application file for complete search history.

(56) References Cited

U.S. PATENT DOCUMENTS 5,755,760 A * 5/1998 Maguire ........... A61M 25/0138
607/122
5,823,955 A * 10/1998 Kuck ..................... A61N 1/056
600/374
(Continued)

FOREIGN PATENT DOCUMENTS

EP  2949283 A1  12/2015

OTHER PUBLICATIONS

International Search Report and Written Opinion for International Application No. PCT/IB2018/056219, dated Dec. 4, 2018, 11 pages.
(Continued)

*Primary Examiner* — Jaymi E Della
(74) *Attorney, Agent, or Firm* — Armstrong Teasdale LLP

(57) ABSTRACT

A method of navigating a catheter to a target location in an anatomical structure of a patient includes inserting a portion of a catheter into the patient. The catheter includes an elongate shaft having a proximal and a distal end, and a loop subassembly coupled to the distal end. The loop subassembly includes a loop coupled to the distal end and positioned parallel to the elongate shaft, and electrodes disposed on the loop. The method includes positioning one of a portion of the loop subassembly and a portion of the distal end of the elongate shaft in contact with a surface of the anatomical structure a distance from the target location, and translating the loop subassembly toward the target location with the one of the portion of the loop subassembly and the portion of the distal end of the elongate shaft in contact with the surface of the anatomical structure.

15 Claims, 15 Drawing Sheets

(52) U.S. Cl.
    CPC ............. *A61B 2018/00577* (2013.01); *A61B 2018/00613* (2013.01); *A61B 2018/1407* (2013.01); *A61B 2018/1467* (2013.01)

(56) References Cited

U.S. PATENT DOCUMENTS

| | | | |
|---|---|---|---|
| 5,921,924 | A | 7/1999 | Avitall |
| 6,071,274 | A | 6/2000 | Thompson et al. |
| 6,613,046 | B1 * | 9/2003 | Jenkins .............. A61B 18/1492 600/374 |
| 9,480,521 | B2 | 11/2016 | Kim et al. |
| 2001/0007927 | A1 * | 7/2001 | Koblish ............. A61B 18/1492 600/585 |
| 2006/0241366 | A1 * | 10/2006 | Falwell ................ A61B 5/6856 606/41 |
| 2010/0191232 | A1 | 7/2010 | Boveda |
| 2012/0232374 | A1 | 9/2012 | Werneth et al. |
| 2015/0196357 | A1 * | 7/2015 | Chen ................. A61B 18/1206 606/41 |
| 2015/0305805 | A1 * | 10/2015 | Xiao ................. A61B 18/1206 606/39 |

OTHER PUBLICATIONS

Communication pursuant to Article 94(3) EPC in related EP Patent Application No. 18772869.6, dated Nov. 26, 2020, 4 pages.

* cited by examiner

MEDICAL CATHETERS, SYSTEMS INCLUDING MEDICAL CATHETERS, AND METHODS OF POSITIONING MEDICAL CATHETERS

This application is the national stage entry of PCT/IB2018/056219, filed on Aug. 17, 2018, which claims priority to U.S. Provisional Application Ser. No. 62/547,502, filed Aug. 18, 2017, which are incorporated by reference in their entirety.

BACKGROUND OF THE DISCLOSURE

A. Field of the Disclosure

The present disclosure relates generally to medical devices that are used in the human body. In particular, in many embodiments, the present disclosure relates to medical catheters, systems including medical catheters, and methods of positioning medical catheters within the human body.

B. Background

Medical devices, such as catheters, are used in a variety of diagnostic and/or therapeutic medical procedures. Typically in a procedure, a catheter is manipulated through a patient's vasculature to, for example, a patient's heart. The catheter carries one or more electrodes that may be used for mapping, navigation, ablation, electroporation, diagnosis, and/or to perform other functions. Once at an intended site, treatment may include radio frequency (RF) ablation, cryoablation, electroporation, lasers, chemicals, high-intensity focused ultrasound, etc. As readily apparent, such treatment requires precise control of the catheter during manipulation to, from, and at the treatment site, which can invariably be a function of a user's skill level.

At least some medical procedures use a hoop catheter (also sometimes referred to as a loop catheter), which includes a substantially circular loop at a distal end of the catheter with the catheter's electrodes disposed around the loop. Such catheters are generally constructed with the loop substantially perpendicular to the shaft of the catheter. The catheter's shaft typically connects to the loop and transitions to the perpendicular plane of the loop either at the center of the loop or along an edge of the loop. An example of such a catheter configuration is shown in FIGS. 15 and 16. Navigating such perpendicular loop catheters through the human body is often difficult and requires possession of significant skill by the practitioner operating the catheter. For example, as shown in FIG. 16, to enter an opening from a chamber of the heart, a practitioner typically needs to navigate the loop of the catheter to a position directly above the opening and move the loop in a straight line directly through the opening. Such navigation can be difficult particularly in locations with limited space to maneuver, relatively tight turns, and the like. Perpendicular loop catheters are sometimes also difficult to position in a desired relationship with an anatomical feature, such as with its electrodes in contact with a particular anatomical surface.

BRIEF SUMMARY OF THE DISCLOSURE

The present disclosure generally relates to medical catheters, systems including medical catheters, and methods of navigating medical catheters through a human body.

In one embodiment, the present disclosure is directed to a method of navigating a catheter to a target location in an anatomical structure of a patient. The method includes inserting a portion of a catheter into the patient. The catheter includes an elongate shaft having a proximal end and a distal end, and a loop subassembly coupled to the distal end of the elongate shaft. The loop subassembly includes a loop coupled to the distal end of the elongate shaft and positioned parallel to the elongate shaft, and a plurality of electrodes disposed on the loop. The method includes positioning one of a portion of the loop subassembly and a portion of the distal end of the elongate shaft in contact with a surface of the anatomical structure a distance from the target location, and translating the loop subassembly toward the target location with the one of the portion of the loop subassembly and the portion of the distal end of the elongate shaft in contact with the surface of the anatomical structure.

In another embodiment, the present disclosure is directed to a catheter including an elongate shaft having a proximal end and a distal end, and a loop subassembly coupled to the distal end of the elongate shaft. The loop subassembly includes a loop coupled at a distal portion of the loop to the distal end of the elongate shaft and positioned parallel to the elongate shaft, and a plurality of electrodes disposed on the loop.

In another embodiment, the present disclosure is directed to a medical system including a computer system, at least one medical subsystem, and a catheter. The at least one medical subsystem is coupled to the computer system and includes one of an ablation generator, an electrophysiology monitor, and a localization and navigation system. The catheter includes an elongate shaft having a proximal end and a distal end, a handle coupled to the proximal end of the elongate shaft, and a loop subassembly coupled at a distal portion of the loop to the distal end of the elongate shaft. The loop subassembly includes a loop coupled the distal end of the elongate shaft and positioned parallel to the elongate shaft, and a plurality of electrodes disposed on the loop.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

The present disclosure relates generally to medical devices that are used in the human body. In particular, in many embodiments, the present disclosure relates to medical catheters, systems including medical catheters, and methods of positioning medical catheters within the human body. The disclosed embodiments may lead to improved navigability through the human body and/or improved placement of a catheter relative to a desired target location, such as within a vein. It is contemplated, however, that the described features and methods of the present disclosure as described herein may be incorporated into any number of systems as would be appreciated by one of ordinary skill in the art based on the disclosure herein.

Figure 1:
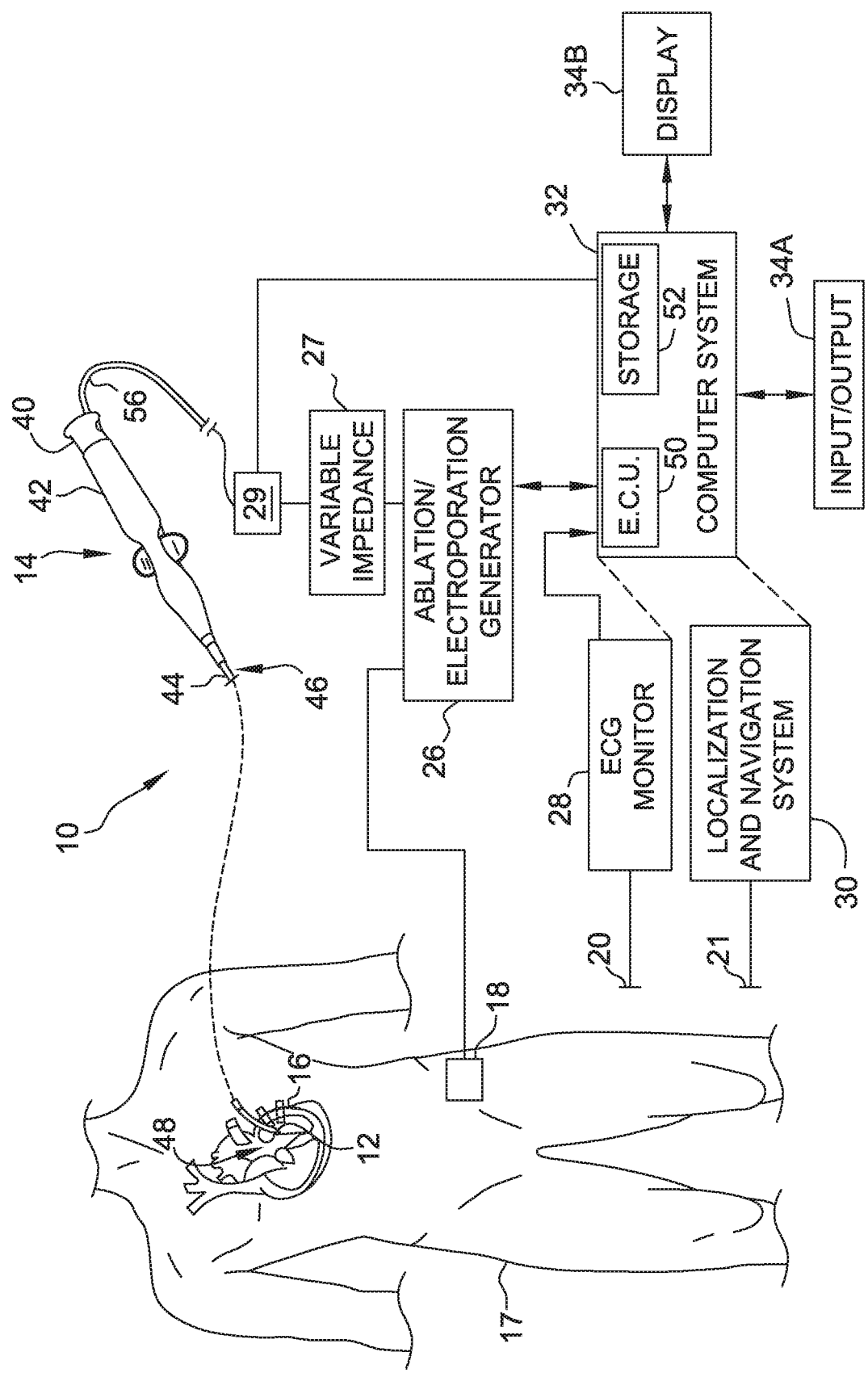
FIG. 1 is a schematic and block diagram view of a medical system incorporating embodiments of the present disclosure.

Referring now to the drawings, FIG. 1 is a diagrammatic and block diagram view of a system 10 for diagnostic purposes, anatomical mapping, electroporation therapy, and/or ablation therapy. In general, the various embodiments include an electrode assembly disposed at the distal end of a catheter. As used herein, "proximal" refers to a direction toward the end of the catheter near the clinician and "distal" refers to a direction away from the clinician and (generally) inside the body of a patient.

System 10 includes a catheter electrode assembly 12 including at least one catheter electrode configured to be used as described below. Electrode assembly 12 is incorporated as part of a medical device such as a catheter 14 for diagnostic, mapping, and/or therapeutic procedures. For example, electrode assembly 12 may be used for electroporation therapy of tissue 16 in a body 17 of a patient. In the illustrative embodiment, tissue 16 comprises heart or cardiac tissue. It should be understood, however, that embodiments may be used to conduct electroporation therapy with respect to a variety of other body tissues.

FIG. 1 further shows a plurality of return electrodes designated 18, 20, and 21, which are diagrammatic of the body connections that may be used by the various sub-systems included in the overall system 10, such as an ablation generator 26, an electrophysiology (EP) monitor such as an ECG monitor 28, a localization and navigation system 30 for visualization, mapping and navigation of internal body structures. In the illustrated embodiment, return electrodes 18, 20, and 21 are patch electrodes. It should be understood that the illustration of a single patch electrode is diagrammatic only (for clarity) and that such sub-systems to which these patch electrodes are connected may, and typically will, include more than one patch (body surface) electrode. In other embodiments, return electrodes 18, 20, and 21 may be any other type of electrode suitable for use as a return electrode including, for example, one or more catheter electrodes. Return electrodes that are catheter electrode may be part of electrode assembly 12 or part of a separate catheter (not shown). System 10 may further include a main computer system 32 (including an electronic control unit 50 and data storage—memory 52), which may be integrated with system 30 in certain embodiments. System 32 may further include conventional interface components, such as various user input/output mechanisms 34a and a display 34b, among other components.

Ablation generator 26 includes radiofrequency (RF) ablation and electroporation generators (not separately shown) to allow system 10 to be used for RF ablation and electroporation. Ablation generator 26 is sometimes referred to herein as ablation/electroporation generator 26. In other embodiments ablation generator may include other ablation generators to allow system to perform any other ablation procedure (such as cryoablation). Ablation generator 26 is configured to energize the electrode element(s) in accordance with an ablation or electroporation energization strategy, which may be predetermined or may be user-selectable. Although illustrated as a single component, generator 26 may include separate ablation and electroporation generators. For electroporation-induced primary necrosis therapy, generator 26 may be configured to produce an electric current that is delivered via electrode assembly 12 as a pulsed electric field in the form of short-duration DC pulses (e.g., a nanosecond to several milliseconds duration, 0.1 to 20 ms duration, or any duration suitable for electroporation) between closely spaced electrodes capable of delivering an electric field strength (i.e., at the tissue site) of about 0.1 to 1.0 kV/cm. The amplitude and pulse duration needed for irreversible electroporation are inversely related. As pulse durations are decreased, the amplitude must be increased to achieve electroporation.

The electroporation portion of generator 26, sometimes also referred to herein as a DC energy source, is a monophasic electroporation generator 26 configured to generate a series DC energy pulses that all produce current in the same direction. In other embodiments, electroporation generator is biphasic or polyphasic electroporation generator configured to produce DC energy pulses that do not all produce current in the same direction. In some embodiments, electroporation generator 26 is a monophasic defibrillator. The defibrillator is configured to output energy in DC pulses at selectable energy levels, such as fifty joules, one hundred joules, two hundred joules, and the like. Other embodiments may have more or fewer energy settings and the values of the available setting may be the same or different. For successful electroporation, some embodiments utilize the two hundred joule output level. Electroporation generator 26 may output a DC pulse having a peak magnitude of about between about negative one kilovolt (kV) and about negative two kV at the two hundred joule output level. In some embodiments, electroporation generator 26 outputs a DC pulse having a peak magnitude of about between about negative 1.5 kV and about negative 2.0 kV. Other embodiments may output any other suitable voltage, including a positive voltage. In some embodiments, the monophasic defibrillator is a Lifepak 9 defibrillator available from Physio-Control, Inc., of Redmond, Washington, USA.

When used for ablation procedures, generator 26 outputs radio frequency (RF) energy to catheter 14 through cable 56.

The RF energy leaves catheter 14 through electrodes of electrode assembly 12. The RF energy travels through the patient's body to return electrode 118. The dissipation of the RF energy in the body increases the temperature near the electrodes, thereby permitting ablation to occur. In the exemplary embodiment set forth herein, system 10 is suitable for use in performing renal denervation. It is understood, however, that the system may be used for other treatments without departing from the scope of this disclosure.

A selection interface 29 allows catheter 14 to be selectively connected to electroporation generator 26 (through variable impedance 27) or to localization and navigation system 30 (through computer system 32). Moreover, selection interface 29 is operable to selectively couple different electrodes to electroporation generator or localization and navigation system 30. In the example embodiment, selection interface selectively couple a specific portion (less than all) of the electrodes to the localization and navigation system 30 during mapping, navigation, etc., and couples all of the electrodes to the electroporation generator 26 during electroporation. Other embodiments may selectively couple all electrodes or different groups of electrodes to electroporation generator or localization and navigation system 30.

A variable impedance 27 allows the impedance of the system to be varied to limit arcing from the catheter electrode of catheter 14, particularly during electroporation procedures. Moreover, variable impedance 27 may be used to change one or more characteristics, such as amplitude, duration, pulse shape, and the like, of an output of electroporation generator 26. Although illustrated as a separate component, variable impedance 27 may be incorporated in catheter 14 or generator 26. Variable impedance 27 includes one or more impedance elements, such as resistors, capacitors, or inductors (not shown) connected in series, parallel, or combinations of series and/or parallel. In the illustrated embodiment, variable impedance 27 is connected in series with catheter 14. Alternatively, the impedance elements of variable impedance 27 may be connected in parallel with catheter 14 or in a combination of series and parallel with catheter 14. Moreover, in other embodiments, the impedance elements of variable impedance 27 are connected in series and/or parallel with return electrode 18. Some embodiments include more than one variable impedance 27, each of which may include one or more impedance elements. In such embodiments, each variable impedance 27 may be connected to a different catheter electrode or group of catheter electrodes to allow the impedance through each catheter electrode or group of catheter electrodes to be separately varied. In other embodiments, the impedance of system 10 may not need to be varied and variable impedance 27 may be omitted. Moreover, in some embodiments, variable impedance 27 may be selectively or automatically bypassed when not needed, such as when performing ablation.

In the illustrative embodiment, the variable impedance is a variable resistance. In some embodiments variable impedance 27 includes one or more resistors (not shown) removably connected between generator 26 and catheter 14. The resistors may be connected in series, parallel, or any combination of series and parallel connections to produce a desired system impedance. Some or all of the resistors may be added, removed, or connected differently to vary the system impedance. In some other embodiments, variable impedance 27 is variable resistor, such as a rheostat or a potentiometer. In still other embodiments, variable impedance 27 includes resistors coupled together by one or more switches to allow the resistors to be selectively switched in and out of the connection between generator 26 and catheter 14. Such a variable impedance 27 may also be configured to allow some or all of the resistors to be selectively connected together in series or in parallel with each other. In some embodiments, variable impedance 27 is variable in response to an appropriate control signal from computer system 32. The resistors may be any suitable type of resistor. In all embodiments, the resistors (or other impedance elements) have relatively high energy ratings sufficient to handle the output of generator 26 without being damaged. In some embodiments, variable impedance 27 includes Ohmite PulsEater resistors available from Ohmite Mfg. Co. of Warrenville, IL, USA. With continued reference to FIG. 1, as noted above, catheter 14 may comprise functionality for electroporation and in certain embodiments also an ablation function (e.g., RF ablation). It should be understood, however, that in those embodiments, variations are possible as to the type of ablation energy provided (e.g., cryoablation, ultrasound, etc.).

In the illustrative embodiment, catheter 14 includes a cable connector or interface 40, a handle 42, and a shaft 44 having a proximal end 46 and a distal end 48. Catheter 14 may also include other conventional components not illustrated herein such as a temperature sensor, additional electrodes, and corresponding conductors or leads. The connector 40 provides mechanical and electrical connection(s) for cable 56 extending from generator 26. The connector 40 may comprise conventional components known in the art and as shown is disposed at the proximal end of catheter 14.

Handle 42 provides a location for the clinician to hold catheter 14 and may further provide means for steering or the guiding shaft 44 within body 17. For example, handle 42 may include means to change the length of one or more guidewires extending through catheter 14 to distal end 48 of shaft 44 or other means to steer shaft 44. Moreover, in some embodiments, handle 42 may be configured to vary the shape, size, and/or orientation of a portion of the catheter. Handle 42 is also conventional in the art and it will be understood that the construction of handle 42 may vary. In an alternate exemplary embodiment, catheter 14 may be robotically driven or controlled. Accordingly, rather than a clinician manipulating a handle to advance/retract and/or steer or guide catheter 14 (and shaft 44 thereof in particular), a robot is used to manipulate catheter 14. Shaft 44 is an elongated, tubular, flexible member configured for movement within body 17. Shaft 44 is configured to support electrode assembly 12 as well as contain associated conductors, and possibly additional electronics used for signal processing or conditioning. Shaft 44 may also permit transport, delivery and/or removal of fluids (including irrigation fluids and bodily fluids), medicines, and/or surgical tools or instruments. Shaft 44 may be made from conventional materials such as polyurethane and defines one or more lumens configured to house and/or transport electrical conductors, fluids or surgical tools. Shaft 44 may be introduced into a blood vessel or other structure within body 17 through a conventional introducer. Shaft 44 may then be advanced, retracted and/or steered or guided through body 17 to a desired location such as the site of tissue 16, including through the use of guidewires or other means known in the art.

In some embodiments, catheter 14 is a hoop catheter (also sometimes referred to herein as a loop catheter) having catheter electrodes (not shown in FIG. 1) distributed about one or more hoops at the distal end of shaft 44. The diameter of the hoop(s) (sometimes referred to herein as "loops") may be variable. In some embodiments, the hoop catheter diameter is variable by about ten millimeters (mm) between a minimum diameter and a maximum diameter. The minimum diameter in some embodiments may be selected between about thirteen mm and about twenty mm when the catheter 14 is manufactured. With a ten mm range of variability, such catheters would have a maximum diameter between twenty-three mm and thirty mm. In other embodiments, the hoop diameter is variable between about fifteen mm and about twenty eight mm, between about thirteen mm and about twenty-three mm, or between about seventeen mm and about twenty-seven mm. Alternatively, the catheter may be a fixed diameter hoop catheter or may be variable between different diameters.

In the example embodiment, all catheter electrodes are substantially the same. In some embodiments, catheter 14 has fourteen catheter electrodes. In other embodiments, catheter 14 includes ten catheter electrodes, twenty catheter electrodes, or any other suitable number of electrodes for performing one or more desired procedure. In some embodiments, the catheter electrodes are ring electrodes, such as platinum ring electrodes. Alternatively, the catheter electrodes may be any other suitable type of electrodes, such as single sided electrode or electrodes printed on a flex material. In various embodiments, the catheter electrodes have lengths of 1.0 mm, 2.0 mm, 2.5 mm, and/or any other suitable length.

In other embodiments, catheter 14 includes two or more different types of electrodes. The types of electrodes may differ in size, material, and/or any other suitable characteristic. In some embodiments, catheter 14 has eight first type catheter electrodes and fourteen second type catheter electrodes grouped as seven pairs of second type catheter electrodes. In other embodiments, catheter 14 includes any other suitable number of first and second type catheter electrodes for performing electroporation. Moreover, in other embodiments, the ratio of first type catheter electrodes to second type catheter electrodes is other than 8:14. Ratios of first type catheter electrodes to second type catheter electrodes other than 8:14 may require increasing the size of the shaft of the catheter. In some embodiments, the catheter electrodes are ring electrodes, such as platinum ring electrodes. Alternatively, the catheter electrodes may be any other suitable type of electrodes, such as single sided electrode or electrodes printed on a flex material. In some embodiments, the first type catheter electrodes have lengths of 2.5 mm, and the second type catheter electrodes have lengths of about 1.3 mm. In other embodiments, the first type catheter electrodes have lengths between 2.5 mm and 3.1 mm, between 2.2 mm and 3.1 mm, or any other suitable length for use as described herein. In various embodiments, the second type catheter electrodes have lengths between 1.0 mm and 1.3 mm, between 0.9 mm and 1.5 mm, or any other suitable length for use as described herein.

The localization and navigation system 30 may be provided for visualization, mapping and navigation of internal body structures. System 30 may comprise conventional apparatus known generally in the art (e.g., an EnSite NAVX™ Navigation and Visualization System, commercially available from St. Jude Medical, Inc. and as generally shown with reference to commonly assigned U.S. Pat. No. 7,263,397 titled "Method and Apparatus for Catheter Navigation and Location and Mapping in the Heart," the entire disclosure of which is incorporated herein by reference). In various embodiments, localization and navigation system 30 uses the second type catheter electrodes as bipolar pairs for visualization, mapping and navigation of internal body structures, as described in more detail below. It should be understood, however, that this system is exemplary only and not limiting in nature. Other technologies for locating/navigating a catheter in space (and for visualization) are known, including for example, the CARTO navigation and location system of Biosense Webster, Inc., the AURORA® system of Northern Digital Inc., commonly available fluoroscopy systems, or a magnetic location system such as the gMPS system from Mediguide Ltd. In this regard, some of the localization, navigation and/or visualization system would involve a sensor be provided for producing signals indicative of catheter location information, and may include, for example one or more electrodes in the case of an impedance-based localization system, or alternatively, one or more coils (i.e., wire windings) configured to detect one or more characteristics of a magnetic field, for example in the case of a magnetic-field based localization system.

Figure 2:
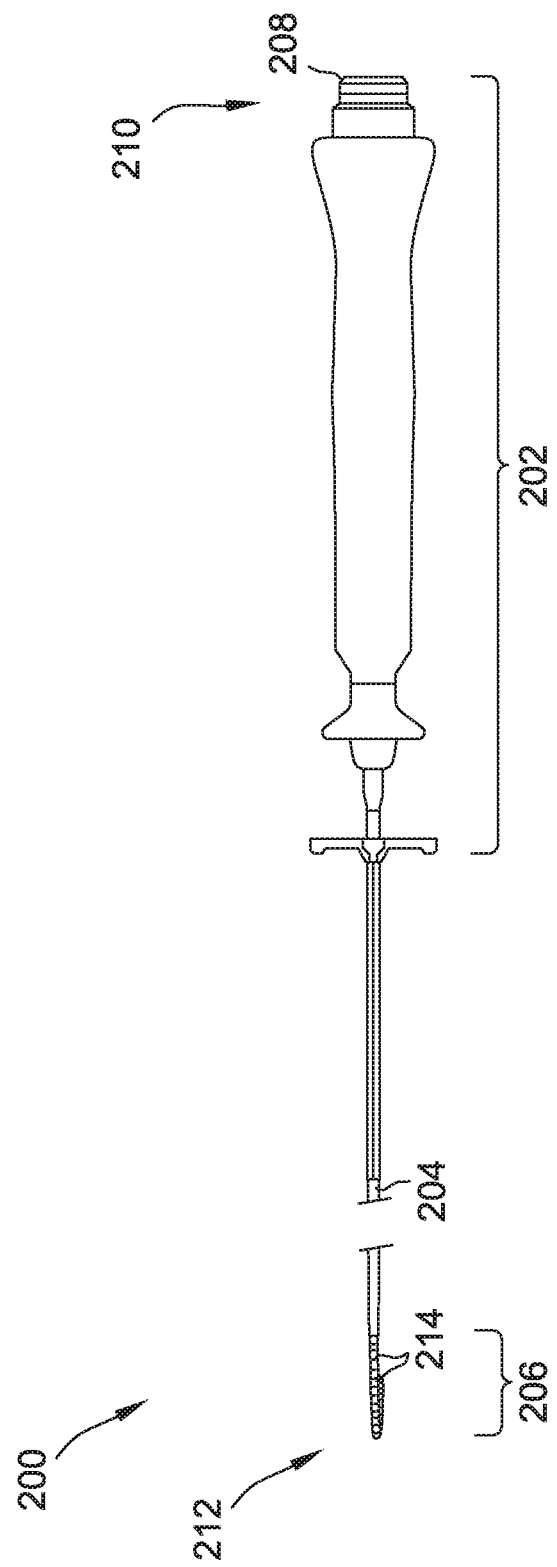
FIG. 2 is a variable diameter, parallel loop, multiple electrode-type catheter.

FIG. 2 is an example parallel loop catheter 200 usable as catheter 14 in system 10. Catheter 200 includes a handle 202, a shaft 204, a distal loop subassembly 206, and a connector 208. Catheter 200 has a proximal end 210 and a distal end 212. As used herein, "proximal" refers to a direction toward the portion of the catheter 200 near the clinician, and "distal" refers to a direction away from the clinician and (generally) inside the body of a patient.

Connector 208 provides mechanical, fluid, and electrical connection(s) for cables, such as, for example, electrical cables (not shown) and/or other components of system 10 (e.g., a visualization, navigation, and/or mapping system, an ablation generator, irrigation source, etc.). Connector 208 is disposed at a proximal end 210 of hoop catheter 200, and handle 202 thereof, in particular. In the example embodiment, connector 208 is a waterproof connector. In other embodiments, connector is water resistant connector. In some embodiments, connector 208 is not itself waterproof, but includes a waterproof element to protect the connector from liquids and moisture, such as a waterproof or water resistant sheath. In some embodiments, connector 208 further includes an insulator or insulating material (not shown), such that connector 208 is suitable for conducting voltages in the range of one thousand volts and electrical current in the range of ten amps. In the example embodiment, connector 208 is used to couple catheter 200 to generator 26.

Handle 202, which is disposed at proximal end 210 of shaft 204, provides a location for the clinician to hold catheter 200 and may further provide means for steering or guiding shaft 204 within the body of the patient. Handle 202 may include means to change the length of a steering wire extending through catheter 200 to distal end 212 of shaft 204 to steer shaft 204. In other embodiments, catheter 200 may be robotically driven or controlled. Accordingly, rather than a clinician manipulating a handle to steer or guide catheter 200 and shaft 204 thereof, in such an embodiments, a robot is used to manipulate catheter 200. In various embodiments, handle 202 is a FLEXABILITY Uni-D handle with modifications configured to increase pull wire travel. Handle 202 may further include an 8 F shaft lug and flush port plug. Handle 202 is at least partially hollow to define an interior channel (not shown) therethrough.

Shaft 204 is an elongate, tubular, flexible member configured for movement within body 17. In the example embodiment, shaft 204 is a size 8 F shaft. Other embodiments may include a different size shaft 204. A pull wire (not shown) for adjusting the diameter of the hoop and electrical conductors (not shown) connected between electrodes at distal end 212 and connector 208 are disposed within an interior channel (not shown) defined by shaft 204. Shaft 204 may also permit transport, delivery, and/or removal of fluids (including irrigation fluids, cryogenic ablation fluids, and bodily fluids), medicines, and/or surgical tools or instruments. Shaft 204 may be made from conventional materials such as polyurethane, and defines one or more lumens configured to house and/or transport electrical conductors, fluids, or surgical tools. Shaft 204 may be introduced into a blood vessel or other structure within the body 17 (shown in FIG. 1) through a conventional introducer. Shaft 204 may then be steered or guided through body 17 to a desired location, such as the heart, using means well known in the art. Shaft 204 houses electrode wires (not shown in FIG. 2) for carrying electrical current to electrodes 214. Electrode wires extend between handle 202 and electrodes 214 within an interior portion of shaft 204. To this end, shaft 204 may include an insulator or insulating material. For example, shaft 204 may be packed with an insulation material and/or a cylindrical layer of insulation material may be circumferentially disposed within an interior portion of shaft 204. In some embodiments, the thickness and material characteristics of such insulation are selected to configure shaft 204 for safe use with voltage and current in the range of one thousand volts and/or ten amperes.

Catheter electrodes 214 mounted on distal loop subassembly 206 may be used for a variety of diagnostic and therapeutic purposes including, for example and without limitation, electroporation, electrophysiological studies, pacing, cardiac mapping and navigation, and ablation. In some embodiments, catheter electrodes 214 include two types of electrodes configured for selective use as electroporation electrodes and navigation/mapping electrodes. For example, a first type of catheter electrodes 214 are configured for selective use for electroporation, while a second type of catheter electrodes 214 are configured for selective use for electroporation and a location or position sensing function (e.g., mapping or navigation). More particularly, the second type of catheter electrodes 214 may be selectively used as a positioning sensor(s) that provides information relating to the location (position and orientation) of catheter 200, and distal end 212 of shaft 204 thereof, in particular, at certain points in time. Accordingly, as catheter 200 is moved along a surface of a structure of interest of a heart (shown in FIG. 1) and/or about the interior of the structure, the sensor(s) can be used to collect location data points that correspond to the surface of, and/or other locations within, the structure of interest. These location data points can then be used by, for example, a model construction system, in the construction of a three-dimensional model of the structure of interest. Other embodiments include a single type of electrode 214, which may be used for a single purpose or may be used for multiple purposes.

Figure 3:
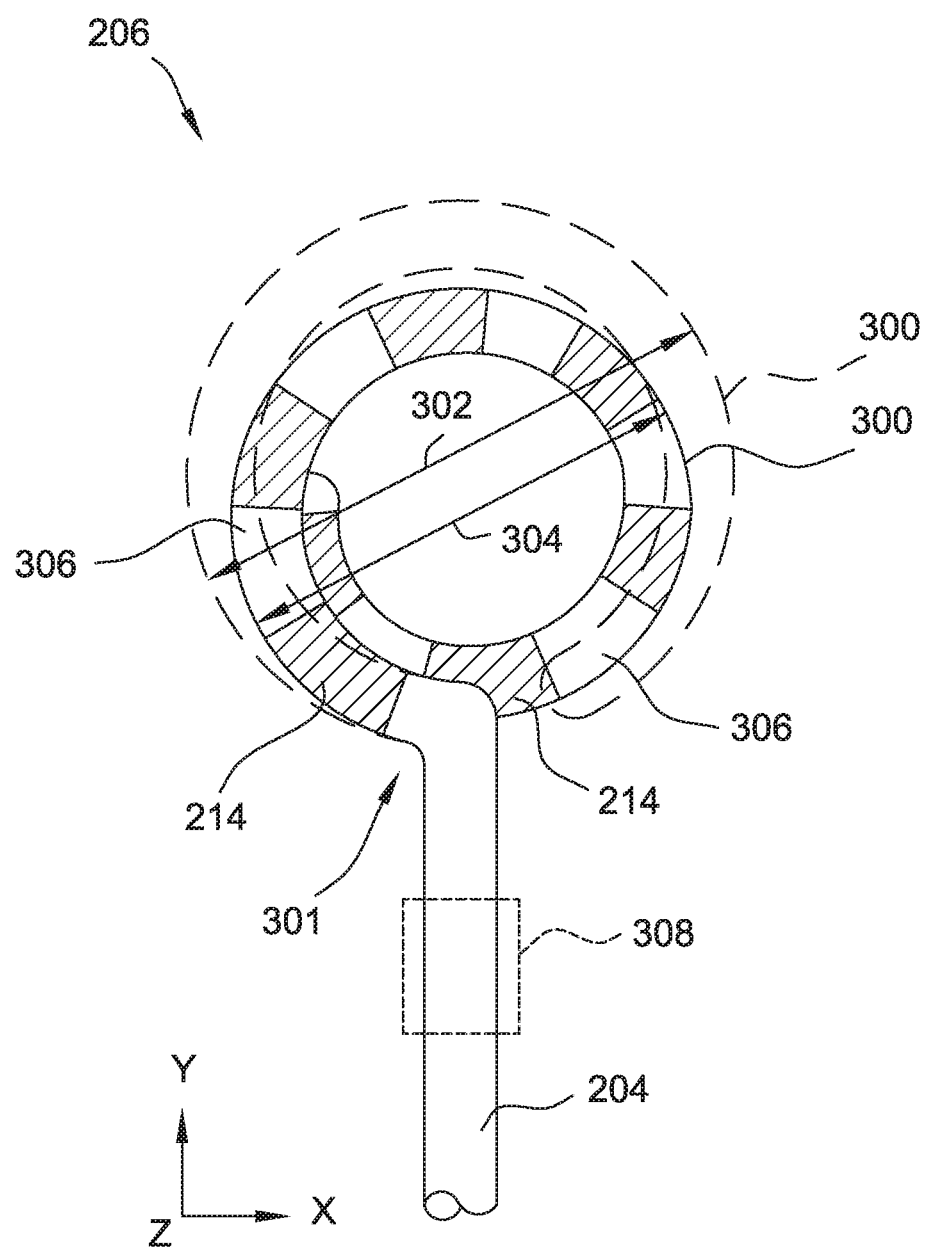
FIG. 3 is a top view of a parallel loop, distal loop subassembly for in an expanded and a contracted position use with the catheter of FIG. 2.
Figure 4:
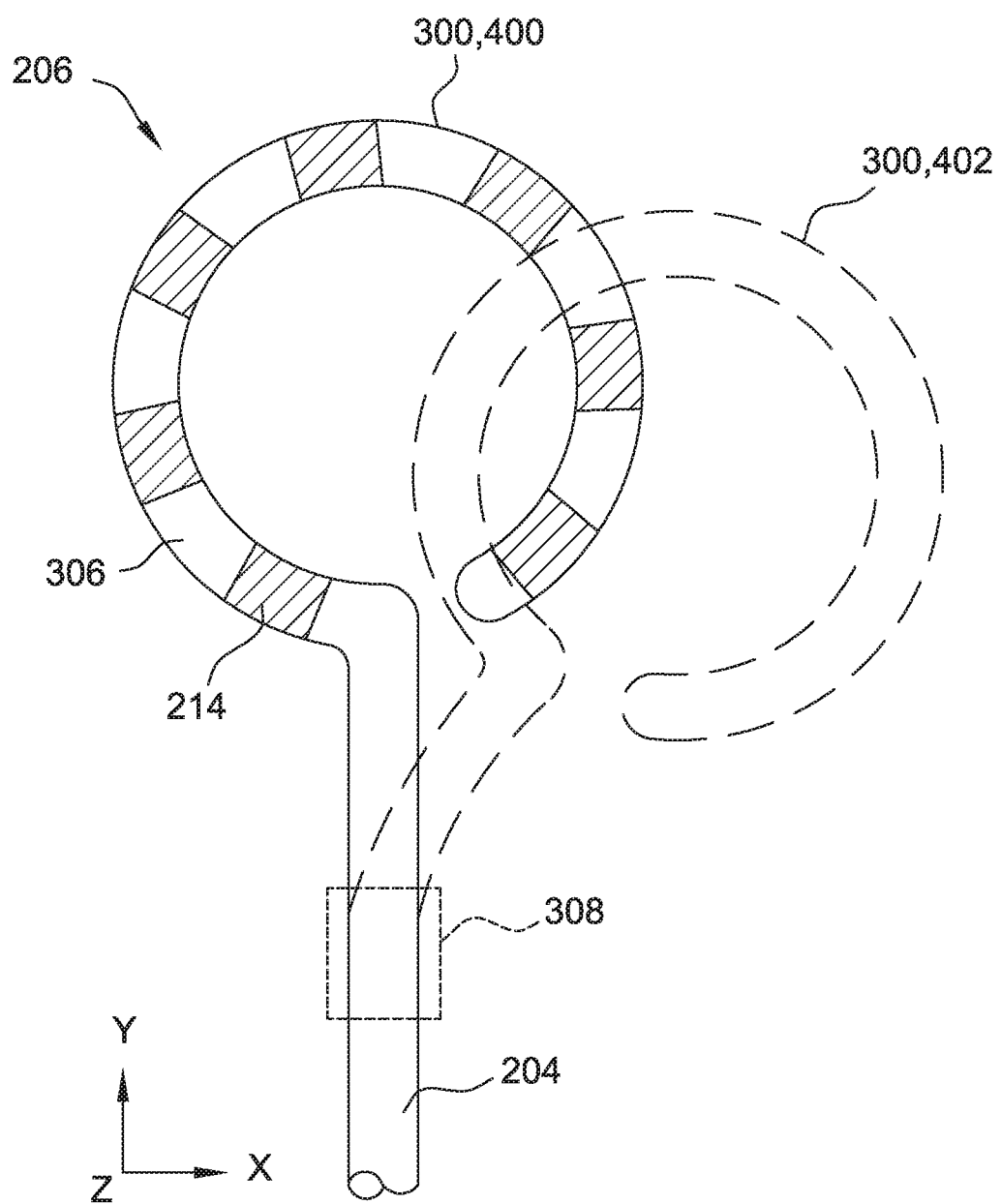
FIG. 4 is a top view of the distal loop subassembly of FIG. 3 in a neutral position and deflected in a first plane.
Figure 5:
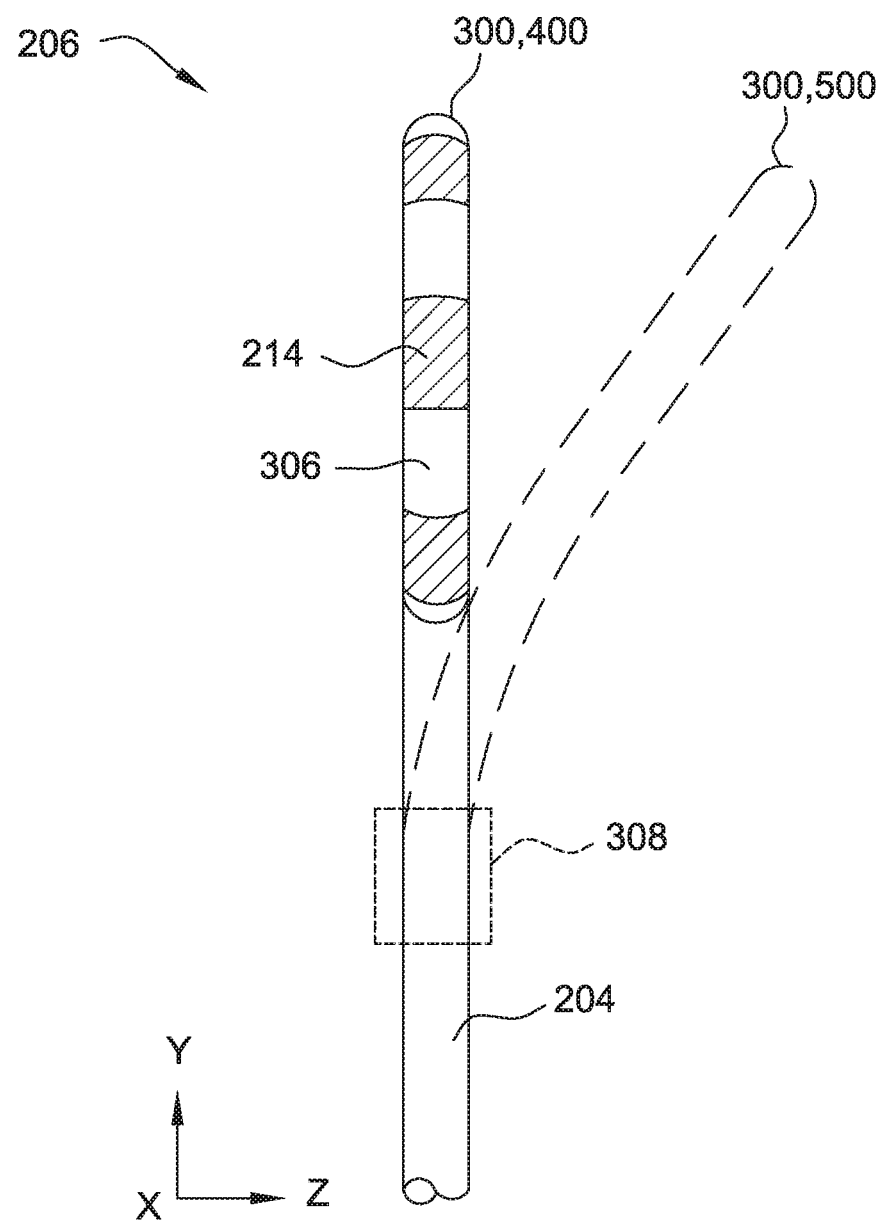
FIG. 5 is a side view of the distal loop subassembly of FIG. 3 in a neutral position and deflected in a second plane.

Distal loop subassembly 206 will be further described with reference to FIGS. 3, 4, 5, and 6. FIG. 3 is a simplified top view of distal loop subassembly 206 with variable diameter loop 300 at an expanded diameter and a retracted diameter. FIG. 4 is a simplified top view of distal loop subassembly 206 with variable diameter loop 300 in a neutral position and deflected in a first plane. FIG. 4 is a simplified side view of distal loop subassembly 206 with variable diameter loop 300 in a neutral position and deflected in a second plane. FIG. 5 is a simplified isometric view of distal loop subassembly 206 with variable diameter loop 300 in a neutral position and deflected in the second plane.

With reference initially to FIG. 3, loop 300 includes a portion of shaft 204, which is connected to a proximal portion 301 of the circumference of loop 300. Loop 300 is variable between an expanded (also referred to as "open")
diameter 302 (shown in ghost in FIG. 3) and a retracted (also referred to as "closed") diameter 304. In the example embodiment, the expanded diameter 302 is twenty seven mm and the retracted diameter 304 is fifteen mm. In other embodiments, the diameter may be variable between any suitable open and closed diameter. Alternatively, distal loop subassembly 206 may include a fixed diameter loop.

Variable diameter loop 300 is illustrated in simplified form in FIGS. 3-6 with seven catheter electrodes 214 spaced around the circumference of variable diameter loop 300. Some exemplary embodiments include twenty-two catheter electrodes 214. In some embodiments, loop 300 has fourteen catheter electrodes 214. In other embodiments, loop 300 includes ten catheter electrodes 214, twenty catheter electrodes 214. Other embodiments include any other suitable number of catheter electrodes. Catheter electrodes 214 are platinum ring electrodes. In some embodiments, catheter electrodes 214 are configured to conduct and/or discharge electrical current in the range of one thousand volts and/or ten amperes to be suitable for use in electroporation. In other embodiments, variable diameter loop 300 may include any suitable number of catheter electrodes 214 made of any suitable material. In the example embodiment, all electrodes 214 are made of the same material. In other embodiments, one or more electrodes 214 may be made from different materials than the other catheter electrodes 214. Catheter electrodes 214 may comprise any catheter electrode suitable to conduct the voltage and/or current required for the particular purpose(s) for which it will be used (e.g., electroporation, ablation, navigation/mapping, etc.). Adjacent catheter electrodes 214 are separated from each other by an insulated gap 306.

In the example embodiment, each catheter electrode 214 is substantially the same as each other catheter electrode 21 and the catheter electrodes are ring electrodes, such as platinum ring electrodes. Alternatively, the catheter electrodes may be any other suitable type of electrodes, such as single sided electrode or electrodes printed on a flex material. In various embodiments, catheter electrodes 214 have lengths of 1.0 mm, 2.0 mm, 2.5 mm, and/or any other suitable length.

In other embodiments, catheter electrodes 214 include first type catheter electrodes and second type catheter electrodes. The two types of catheter electrodes have at least one different characteristic, such as size, shape, material, and the like. In some embodiments, the two types of electrodes alternate along loop 300. In other embodiments, the two types alternate along loop 300, with pairs of second type catheter electrodes positioned adjacent a first type catheter electrodes. The sequence of alternating electrodes begins and ends, in some such embodiments, with a first type catheter electrode, and each pair of second type catheter electrodes is positioned between two first type catheter electrodes. In other embodiments, the sequence of alternating electrodes 214 may begin or end with second type catheter electrodes. In some embodiments first type catheter electrodes are separated from adjacent second type catheter electrodes by a first insulated gap having a length different than a second insulated gap separating second type catheter electrodes from adjacent second type catheter electrodes.

Figure 13:
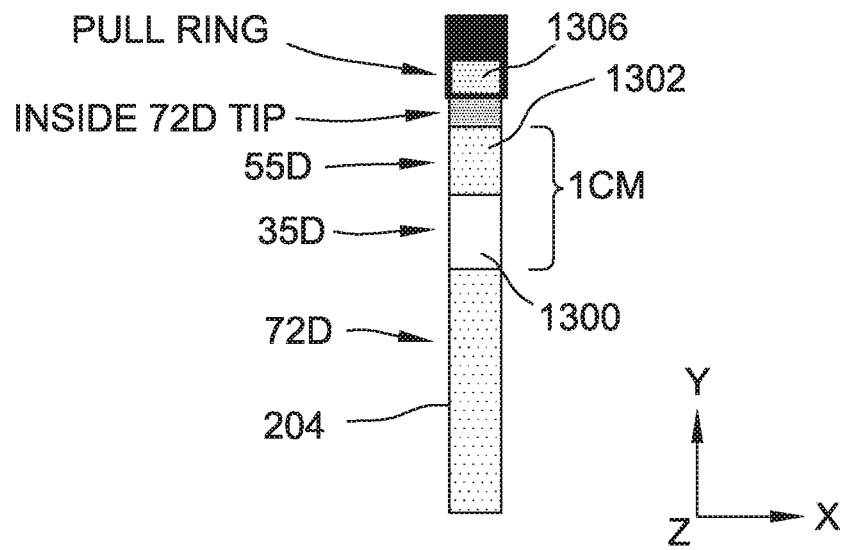
FIG. 13 is a top view of the material construction of a portion of the distal loop subassembly of FIG. 3.
Figure 14:
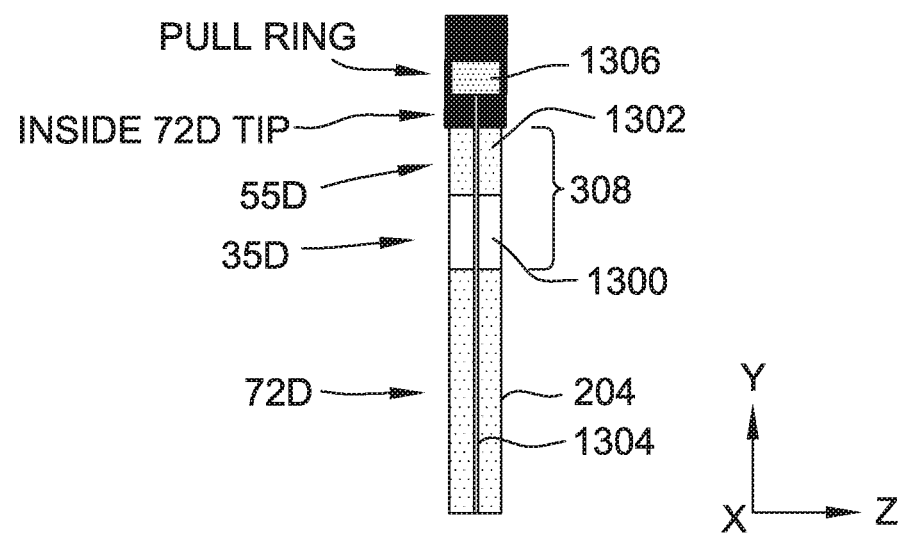
FIG. 14 is a side view of the material construction of a portion of the distal loop subassembly of FIG. 3.

Distal loop subassembly 206 is configured to allow loop 300 to be controllably deflected in two planes. Distal loop subassembly 206 includes a deflectable section (sometimes also referred to as a joint or hinge) 308 at which shaft 204 is deflectable to move loop 300 relative to the undeflected portion of shaft 204 (i.e., the portion of shaft proximal deflectable section 308. Although a single deflectable portion is illustrated, subassembly 206 may include more than one deflectable section and/or the deflectable section may be located closer or further away from loop 300. Generally, pairs of pull wires pass down the length of shaft 204 and distal loop subassembly 206 on opposite sides of shaft 204 and are fixedly connected to a point at the distal end of catheter 200. The pull wires lie in a plane. Tensioning/shortening one wire and/or lengthening the other wire (such as by using an actuator on handle 202) will cause shaft 204 and/or distal loop subassembly 206 to deflect toward the shorter pull wire with the deflection point being or bend primarily at deflectable section 308. Other embodiments may include a single pull wire for each plane of deflection. The location of the deflection is configured, by varying the rigidity of materials along shaft 204 and distal loop subassembly 206 to include more flexible material in the region(s) in which deflection is desired. FIGS. 13 and 14 are top and side views, respectively, of a portion of shaft 204 showing example material construction of deflectable section 308. As can be seen, shaft 204 is constructed generally of material having a nominal shore hardness of 75 D. Deflectable section 308 includes a first section 1300 having a nominal shore hardness of 35D and second section 1302 having a nominal shore hardness rating of 55 D. One of two opposing pull wires 1304 connected to pull ring 1306 for deflecting the loop 300 in the X-Y plane is visible in FIG. 14. In FIG. 13, pull wires 1304 are not visible, but are located on the left and right sides of shaft 204. Additional details of the construction and operation of deflectable medical shafts suitable for use in catheter 200 are described in U.S. Patent Application Publication No. US2007/0299424, and U.S. Pat. Nos. 7,691,095, 7,914,515 and 8,734,699, each of which is incorporated herein by reference in its entirety.

In FIG. 4, loop 300 is shown in a neutral (or undeflected) position 400 and is shown, in ghost, in a deflected position 402. Neutral position 400 is the natural position of the loop 300 relative to the rest of distal loop subassembly 206 and shaft 204 (shown in FIG. 2). In deflected position 402, loop 300 is deflected to the right (relative to neutral position 400 as viewed in FIG. 4) within the X-Y plane. Although not shown, loop 300 may also be deflected to the left within the X-Y plane. In other embodiments, distal loop subassembly 206 is configured for deflection in the X-Y plane in only one direction relative to neutral position 400. In the example embodiment, the maximum deflection of loop 300 in each direction is about forty-five degrees from neutral position 400. In other embodiments, loop 300 is deflectable in each direction up to a maximum between about fifteen degrees and about twenty degrees from neutral position 400. Alternatively, the maximum deflection in each direction may be any other suitable angle of deflection.

Figure 6:
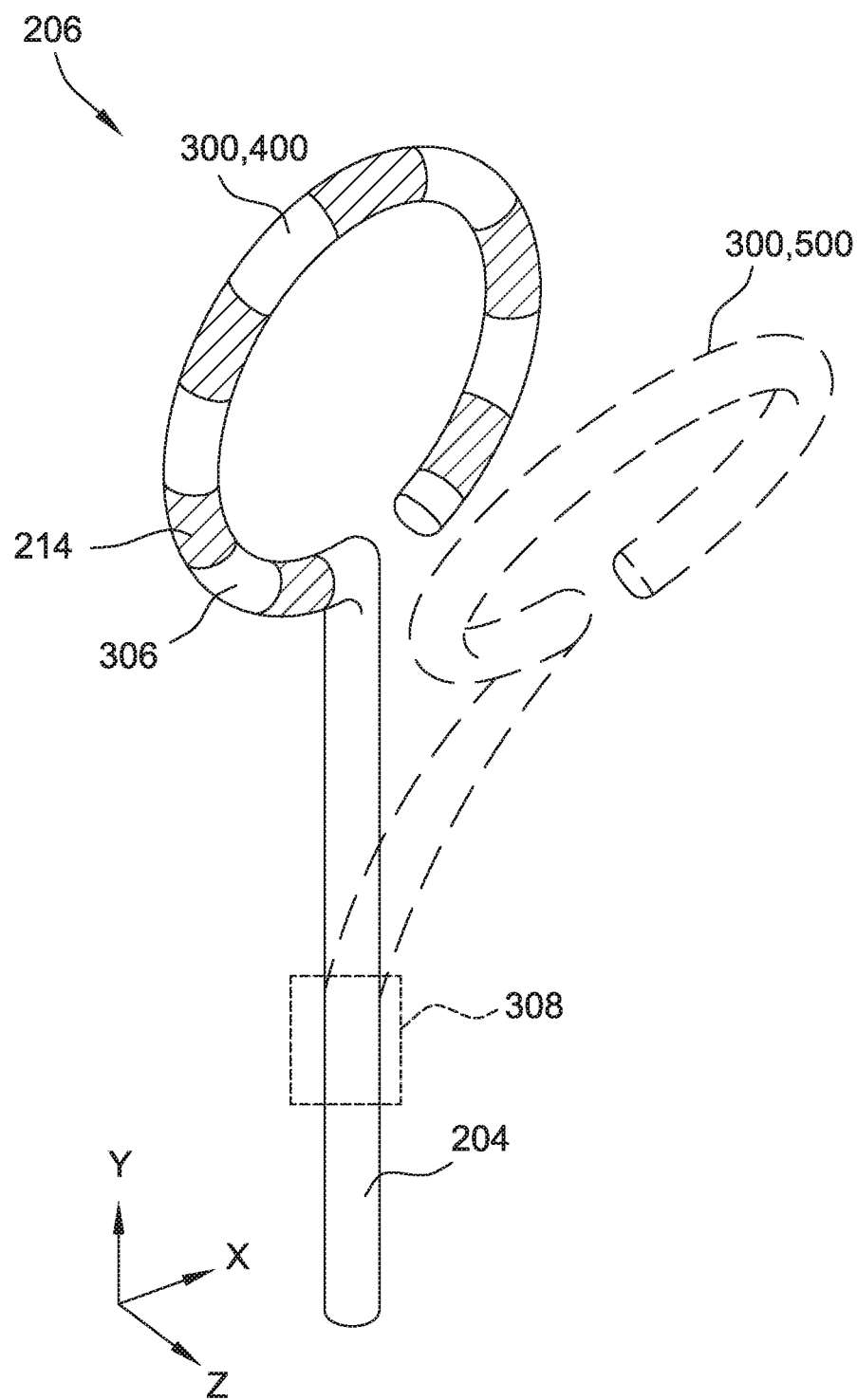
FIG. 6 is an isometric view of the distal loop subassembly of FIG. 3 in a neutral position and deflected in a second plane.

FIG. 5 is a side view of distal loop subassembly 206, in which loop 300 is shown in the neutral (or undeflected) position 400 and is shown, in ghost, in a deflected position 500. In deflected position 500, loop 300 is deflected to the right (relative to neutral position 400 as viewed in FIG. 5) within the Y-Z plane. Although not shown, loop 300 may also be deflected to the left within the Y-Z plane. In other embodiments, distal loop subassembly 206 is configured for deflection in the Y-Z plane in only one direction relative to neutral position 400. FIG. 6 is an isometric view of distal loop subassembly 206, in which loop 300 is shown in the neutral position 400 and is shown, in ghost, in the deflected position 500.

In the example embodiment, loop 300 is deflectable within two orthogonal planes (i.e., the X-Y plane and the Y-Z plane). In other embodiments, loop 300 is deflectable in one plane or more than two planes. Moreover, in some embodiments, loop 300 is deflectable in two or more planes that are not orthogonal to each other.

As can be seen by examination of FIGS. 2-5, in neutral position 400, loop 300 is substantially parallel to shaft 204. Moreover, in this embodiment, loop 300 is positioned coplanar with shaft 204 in neutral position 400. As will be described in more detail below, positioning loop 300 parallel to shaft 204 in the neutral position permits loop 300 to be guided through portions of the body by being positioned adjacent an anatomical structure, such as a wall of the heart, and pushed along the structure, with loop 300 and/or a portion of shaft 204 remaining in contact with the structure to be guided by the surface of the structure.

Figure 7:
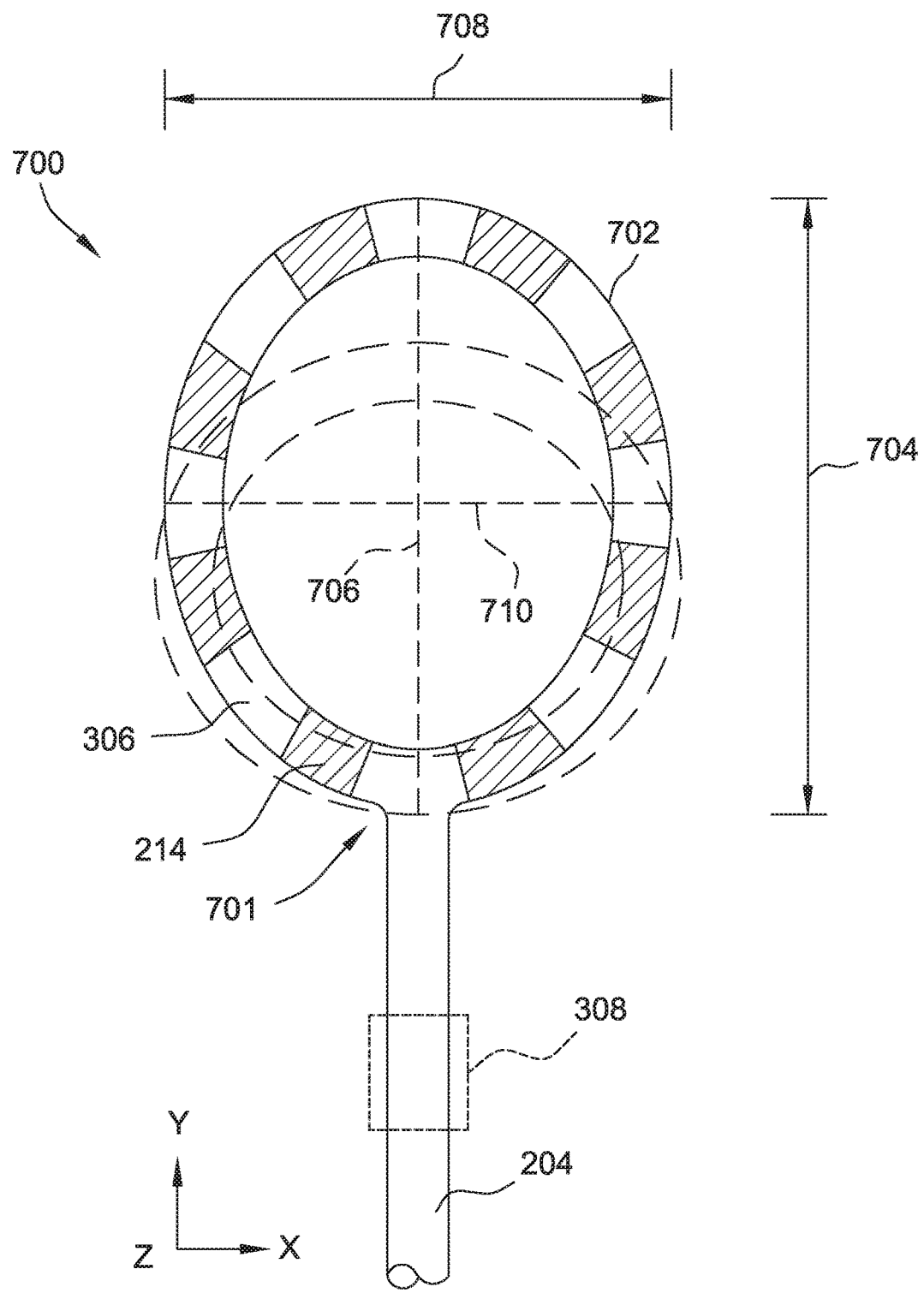
FIG. 7 is a top view of an elliptical parallel loop, distal loop subassembly for use with the catheter of FIG. 2.

FIG. 7 is a top view of another embodiment of a distal loop subassembly 700 suitable for use with catheter 200. Subassembly 700 is similar to distal loop subassembly 206 and common reference numbers indicate common components. Like distal loop subassembly 206, shaft 204 is attached to distal loop subassembly 700 at a proximal portion 701 of distal loop subassembly 700. Unlike distal loop subassembly 206, distal loop subassembly 700 includes a variable diameter, elliptical (also referred to as elongate) loop 702. Elliptical loop 702 has a major diameter 704 along a major axis 706 and a minor diameter 708 along a minor axis 710. When the diameter of elliptical loop 702 is varied by an operator of catheter 200, decreasing major diameter 704 increases minor diameter 708, making the shape of elliptical loop 702 approach a circle (shown in ghost in FIG. 7). In some embodiments, elliptical loop 702 is variable from substantially circular to an ellipse with major diameter 704 approximately seven times the length of minor diameter 708. The variable elliptical shape of loop 702 may allow it to fit better within certain anatomical structures. In particular, elliptical loop 702 may allow for concentric placement within tubular anatomical structures (e.g., veins) with electrodes 214 in contact with the walls of the tubular structure. In an example embodiment targeting use near the antrum, the perimeter length of elliptical loop 702 is about 210 mm, major diameter 704 is variable between about 33 mm and 51 mm, and minor diameter 708 is variable between about 34 mm and 7 mm. In another embodiment for use in smaller locations, the perimeter length of elliptical loop 702 is about 170 mm, major diameter 704 is variable between about 30 mm and 40 mm, and minor diameter 708 is variable between about 25 mm and 10 mm. Other embodiments may have any other suitable perimeter length and corresponding major and minor diameters. Generally, the perimeter length and eccentricity is selected based at least in part on the circumference and eccentricity of one or more target locations for which subassembly 700 will be used. Details of the circumferences and eccentricities of pulmonary veins that may be used for determining a desired perimeter length, major diameter 704, and minor diameter 708 for elliptical loop 702 may be found in AHMED, J., SOHAL, S., MALCHANO, Z. J., HOLMVANG, G., RUSKIN, J. N. and REDDY, V. Y. (2006), Three-Dimensional Analysis of Pulmonary Venous Ostial and Antral Anatomy: Implications for Balloon Catheter-Based Pulmonary Vein Isolation. Journal of Cardiovascular Electrophysiology, 17: 251-255, which is incorporated herein by reference in its entirety.

Figure 8:
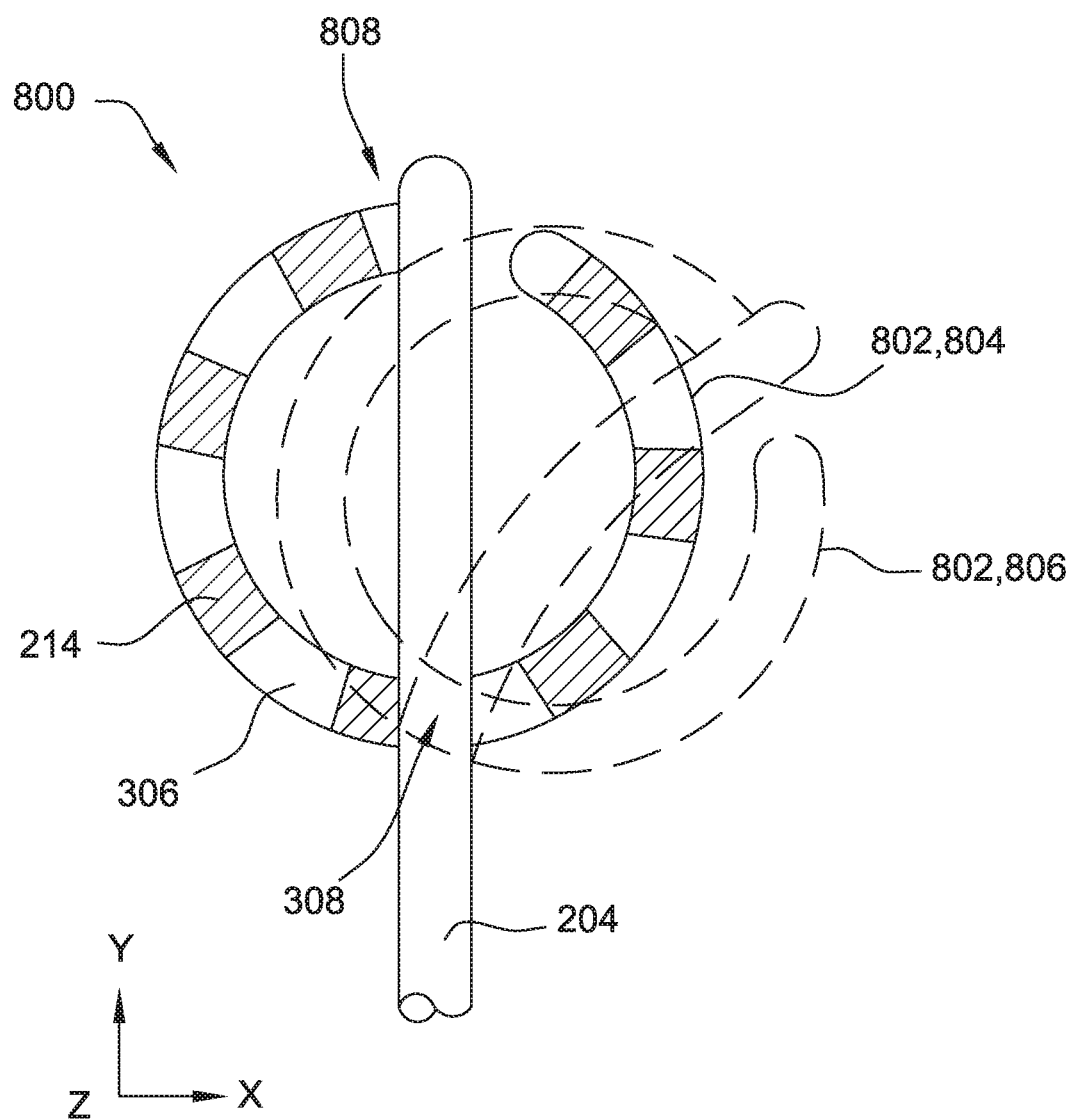
FIG. 8 is a top view of another embodiment of a parallel loop, distal loop subassembly for use with the catheter of FIG. 2.
Figure 9:
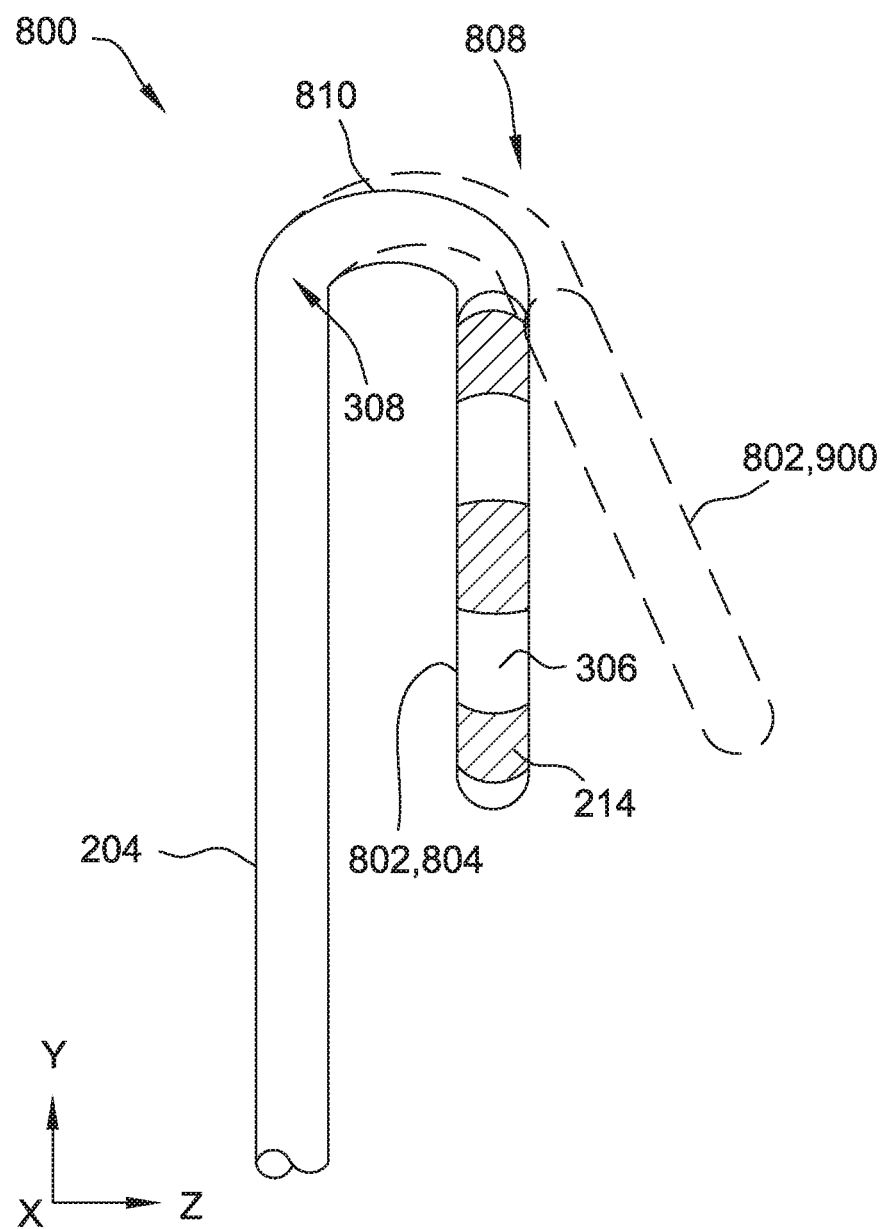
FIG. 9 is a side view of the distal loop subassembly of FIG. 8.
Figure 10:
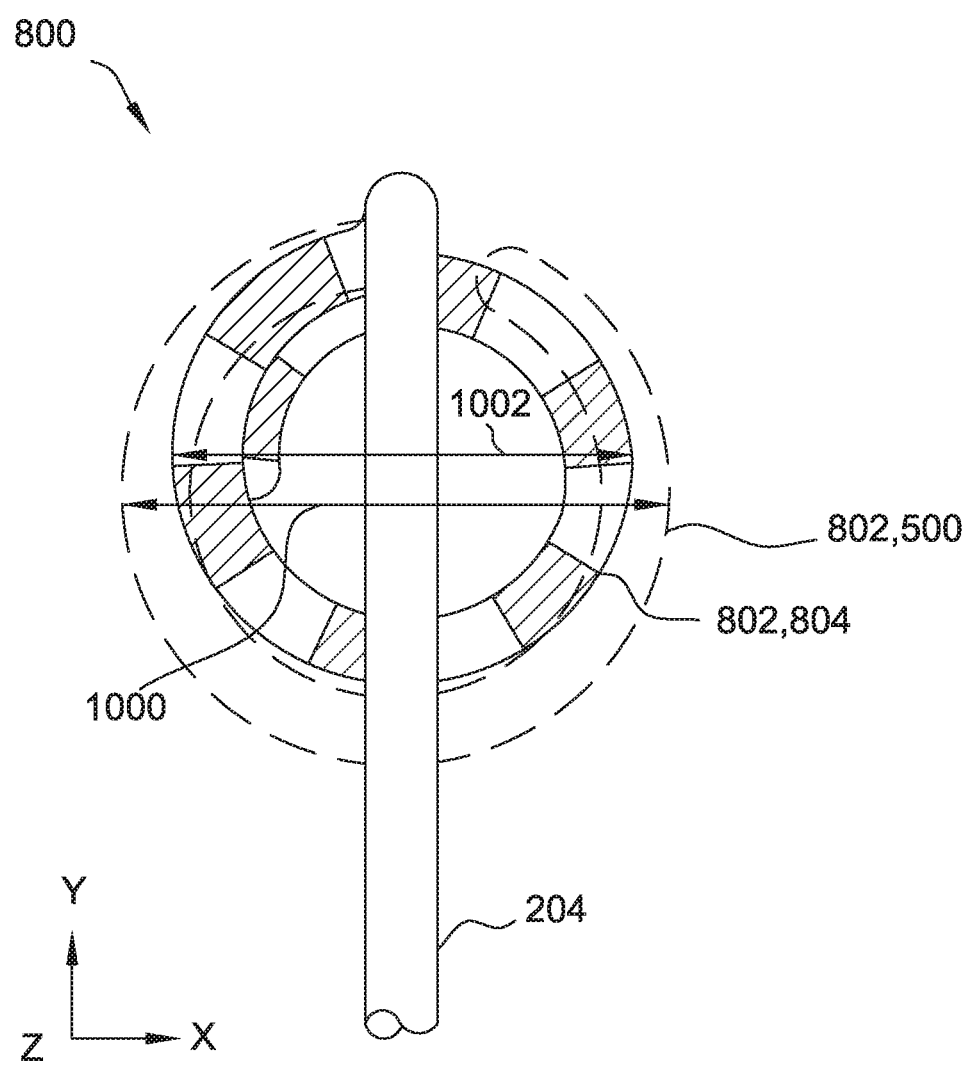
FIG. 10 is a top view of the distal loop subassembly of FIG. 8 in an expanded and retracted position.

Another embodiment of a distal loop subassembly 800 suitable for use with catheter 200 is shown in FIGS. 8-10. FIG. 8 is a simplified top view of distal loop subassembly 800 with variable diameter loop 802 in a neutral position and deflected in a first plane. FIG. 9 is a simplified side view of distal loop subassembly 800 with variable diameter loop 802 in a neutral position and deflected in a second plane. FIG. 10 is a simplified top view of distal loop subassembly 800 with variable diameter loop 802 at an expanded diameter and a retracted diameter. Except as otherwise indicated herein, subassembly 800 and is similar to subassembly 206 and 700. Reference numbers in common with assemblies 206 and/or 700 indicate common components.

In FIG. 8, loop 802 is shown in a neutral (or undeflected) position 804, and is shown, in ghost, in a deflected position 806. Neutral position 400 is the natural position of the loop 300 relative to the rest of distal loop subassembly 800 and shaft 204. In deflected position 806, loop 300 is deflected to the right (relative to neutral position 804 as viewed in FIG. 4) within the X-Y plane. Although not shown, loop 802 may also be deflected to the left within the X-Y plane. In other embodiments, distal loop subassembly 800 is configured for deflection in the X-Y plane in only one direction relative to neutral position 804. In the example embodiment, the maximum deflection of loop 802 in each direction is about forty-five degrees from neutral position 804. In other embodiments, loop 802 is deflectable in each direction up to a maximum between about fifteen degrees and about twenty degrees from neutral position 804. Alternatively, the maximum deflection in each direction may be any other suitable angle of deflection.

FIG. 9 is a side view of distal loop subassembly 800, in which loop 802 is shown in the neutral (or undeflected) position 804 and is shown, in ghost, in a deflected position 500. In deflected position 500, loop 802 is deflected to the right (relative to neutral position 804 as viewed in FIG. 5) within the Y-Z plane. Although not shown, loop 802 may also be deflected to the left within the Y-Z plane. In other embodiments, distal loop subassembly 800 is configured for deflection in the Y-Z plane in only one direction relative to neutral position 804.

As shown in FIG. 10, loop 802 is variable between an expanded (also referred to as "open") diameter 1000 (shown in ghost in FIG. 3) and a retracted (also referred to as "closed") diameter 1002. In the example embodiment, the expanded diameter 1000 is twenty seven mm and the retracted diameter 1002 is fifteen mm. In other embodiments, the diameter may be variable between any suitable open and closed diameter. Alternatively, distal loop subassembly 800 may include a fixed diameter loop.

In the example embodiment, loop 802 is deflectable within two orthogonal planes (i.e., the X-Y plane and the Y-Z plane). In other embodiments, loop 802 is deflectable in one plane or more than two planes. Moreover, in some embodiments, loop 802 is deflectable in two or more planes that are not orthogonal to each other.

As can be seen in FIGS. 8-10, loop 802 is connected to shaft 204 at a distal portion 808 of the circumference of loop 802 by a hinge section 810. In neutral position 804, loop 802 is substantially parallel to shaft 204. However, as best seen in FIG. 9, loop 802 is not coplanar (i.e., it is positioned in a different plane) with shaft 204. In use, this configuration may add additional support to loop 802. The additional support may help navigate the loop 802 over an opening to which loop 802 is being guided and may provide additional resistance force to deflection of loop 802 to engage the loop 802 more completely or uniformly in, for example, a vein. This embodiment may also maneuver to a patient's right superior vein and inferior veins more easily than some known catheters.

Figure 11:
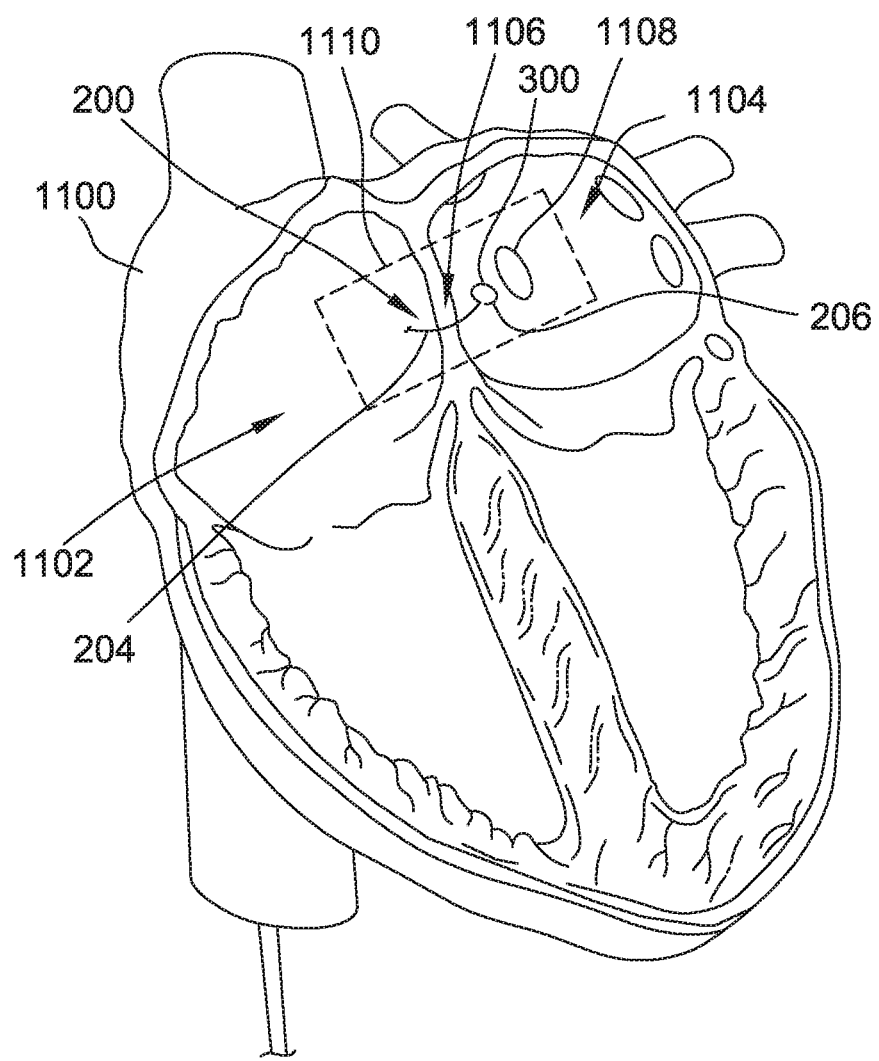
FIG. 11 is a cutaway isometric view of a heart with the distal loop subassembly of FIG. 3 navigating through a chamber of the heart.
Figure 12:
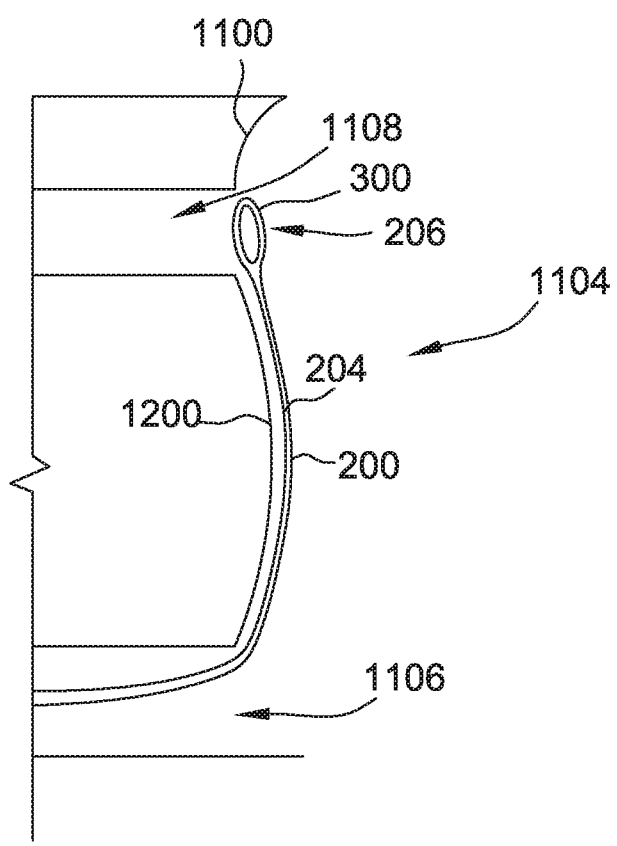
FIG. 12 is a simplified cross-section of a section of FIG. 11.
Figure 15:
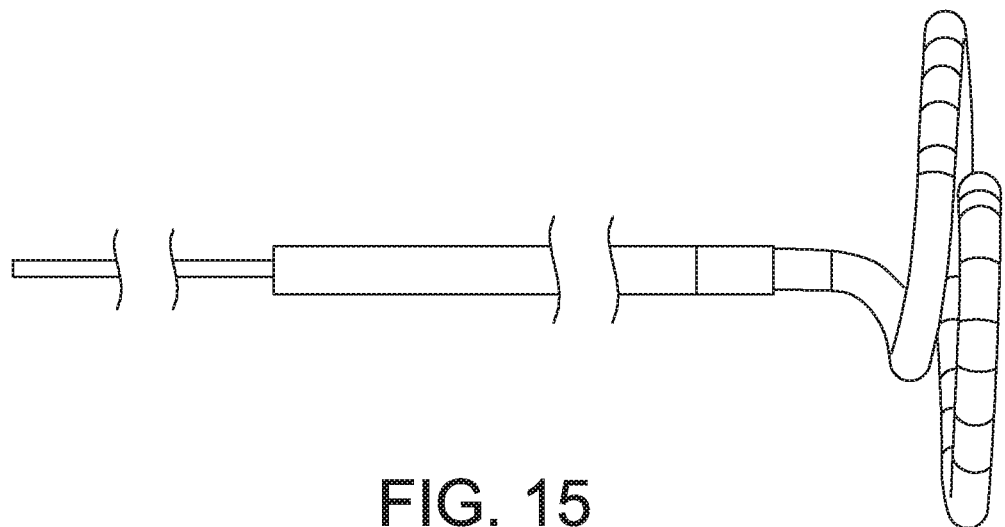
FIG. 15 is a side view of a prior art, perpendicular loop, distal loop subassembly for a catheter.
Figure 16:
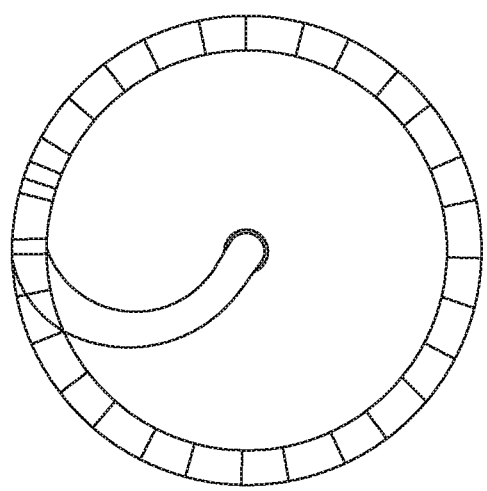
FIG. 16 is a front view of the distal loop subassembly of FIG. 15.
Figure 17:
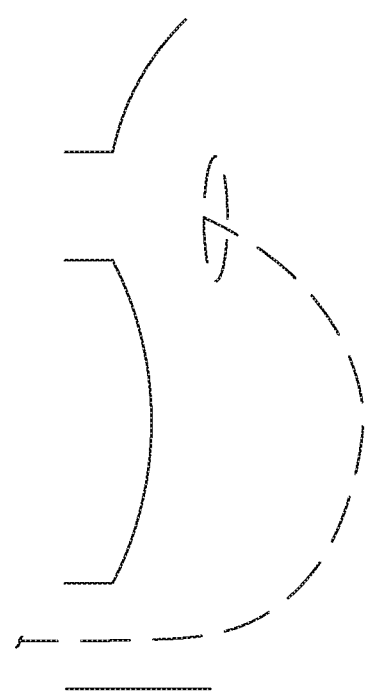
FIG. 17 is a simplified cross-sectional view of the distal loop subassembly of FIG. 15 navigating a same portion of the heart as shown in FIGS. 11 and 12.

As mentioned above, catheter 200, in connection with distal loop subassemblies 206, 700, and 800, may be more easily and/or accurately navigated through an anatomical region because of its ability to slide along a surface of the anatomical region to a desired location or target. FIG. 11 is a partial cutaway view of a heart 1100. Catheter 200 is positioned within heart 1100, passing from the right atrium 1102 to the left atrium 1104 via the fossa 1106. The operator of catheter 200 is directing distal end 212 of catheter (including distal loop subassembly 206) to the right inferior pulmonary vein 1108. FIG. 12 is a simplified cross-sectional view of section 1110 of FIG. 11. As can be seen, at least a portion of catheter shaft 204 and/or loop 300 may slide along the wall of left atrium 1104 to approach right inferior pulmonary vein 1108 from the side, rather than needing to approach from directly above the opening to right inferior pulmonary vein 1108 (as shown for a prior art system in FIG. 15). Thus, to move from to a target location, the subassembly 206, 700, or 800 may be pushed by the catheter operator toward the target location in an anatomical structure (e.g., a heart) while maintaining contact with a surface of the anatomical structure, which will help guide the subassembly toward to the target. The movement of the distal loop subassembly 206, 700, or 800 is generally within a plane defined by the loop of the subassembly (e.g., within the plane of the surface of the page as viewed in FIGS. 3, 4, and 7) or a plane substantially perpendicular to a plane defined by the loop of the subassembly. In some embodiments, the operator may navigate the subassembly 206, 700, or 800 within the plane with a force applied also in the direction of the surface with which it is in contact to maintain contact with the surface and help guide the subassembly 206, 700, or 800 along the surface.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A method of navigating a catheter to a target location in an anatomical structure of a patient, the method comprising:
   inserting a portion of the catheter into the patient, the catheter comprising:
   an elongate shaft having a proximal end and a distal end and defining an axis that extends along a y-direction, wherein the y-direction is perpendicular to an x-direction, and wherein a z-direction is perpendicular to both the x-direction and the y-direction; and
   a loop subassembly coupled to the distal end of the elongate shaft, the loop subassembly comprising:
      a loop coupled to the distal end of the elongate shaft, wherein, in a neutral position, the loop defines a loop plane which is parallel to the axis of the elongate shaft, wherein the loop plane is an x-y plane extending in both the x-direction and the y-direction, wherein the loop plane is positioned in a different plane than the elongate shaft and is spaced from the elongate shaft along the z-direction, and wherein the loop is selectively deflectable, while maintaining a fixed radius of the loop, within the x-y plane that is the loop plane using at least one pull wire extending through the elongate shaft; and
      a plurality of electrodes disposed on the loop;
   positioning one of a portion of the loop subassembly and a portion of the distal end of the elongate shaft in contact with a surface of the anatomical structure a distance from the target location; and
   translating the loop subassembly toward the target location with the one of the portion of the loop subassembly and the portion of the distal end of the elongate shaft in contact with the surface of the anatomical structure.

2. The method of claim 1, wherein translating the loop subassembly toward the target location comprises allowing the surface of the anatomical structure to guide the loop subassembly through contact with the one of the portion of the loop subassembly and the portion of the distal end of the elongate shaft.

3. The method of claim 1, wherein positioning the one of the portion of the loop subassembly and the portion of the distal end of the elongate shaft in contact with the surface of the anatomical structure a distance from the target location comprises positioning the one of the portion of the loop subassembly and the portion of the distal end of the elongate shaft in contact with a wall of a heart of the patient a distance from a target opening in the wall of the patient's heart.

4. The method of claim 3, wherein translating the loop subassembly toward the target location comprises translating the loop subassembly until the loop overlies the target opening in the patient's heart.

5. The method of claim 1, wherein translating the loop subassembly toward the target location comprises pushing the loop subassembly toward the target location while continuously maintaining the contact between the surface of the anatomical structure and the one of a portion of the loop subassembly and a portion of the distal end of the elongate shaft.

6. The method of claim 1, wherein translating the loop subassembly toward the target location comprises translating the loop subassembly within the loop plane.

7. A catheter comprising:
   an elongate shaft having a proximal end and a distal end and defining an axis that extends along a y-direction, wherein the y-direction is perpendicular to an x-direction, and wherein a z-direction is perpendicular to both the x-direction and the y-direction; and
   a loop subassembly coupled to the distal end of the elongate shaft, the loop subassembly comprising:
      a loop coupled at a distal portion of the loop to the distal end of the elongate shaft, wherein, in a neutral position, the loop defines a loop plane which is parallel to the axis of the elongate shaft, wherein the loop plane is an x-y plane extending in both the x-direction and the y-direction, wherein the loop plane is positioned in a different plane than the elongate shaft and is spaced from the elongate shaft along the z-direction, and wherein the loop is selectively deflectable, while maintaining a fixed radius of the loop, within the x-y plane that is the loop plane using at least one pull wire extending through the elongate shaft; and
      a plurality of electrodes disposed on the loop.

8. The catheter of claim 7, wherein the loop comprises a variable diameter loop.

9. The catheter of claim 7, wherein the loop is substantially circular.

10. The catheter of claim 7, wherein the loop is an elliptical loop having a major diameter and a minor diameter.

11. The catheter of claim 8, wherein the variable diameter loop is an elliptical loop having a minor diameter configured to increase in response to a major diameter of the elliptical loop decreasing.

12. The catheter of claim 7, wherein the loop is also selectively deflectable within an additional plane that is perpendicular to the loop plane.

13. A medical system comprising:
   a computer system;
   a medical subsystem coupled to the computer system, the at least one medical subsystem comprising one of an ablation generator, an electrophysiology monitor, or a localization and navigation system; and
   a catheter coupled to the medical subsystem, the catheter comprising:
      an elongate shaft having a proximal end and a distal end and defining an axis;
      a handle coupled to the proximal end of the elongate shaft, the elongate shaft extending along a y-direction, wherein the y-direction is perpendicular to an x-direction, and wherein a z-direction is perpendicular to both the x-direction and the y-direction; and
      a loop subassembly coupled to the distal end of the elongate shaft, the loop subassembly comprising:
         a loop coupled at a distal portion of the loop to the distal end of the elongate shaft, wherein, in a neutral position, the loop defines a loop plane which is parallel to the axis of the elongate shaft, wherein the loop plane is an x-y plane extending in both the x-direction and the y-direction, wherein the loop plane is positioned in a different plane than the elongate shaft and is spaced from the elongate shaft along the z-direction, and wherein the loop is selectively deflectable, while maintaining a fixed radius of the loop, within the x-y plane that is the loop plane using at least one pull wire extending through the elongate shaft; and
         a plurality of electrodes disposed on the loop.

14. The catheter of claim 7, wherein the loop is selectively deflectable away from the neutral position in only one direction.

15. The catheter of claim 7, wherein the loop is selectively deflectable up to forty-five degrees from the neutral position.

\* \* \* \* \*